United States Patent [19]

Szantay et al.

[11] 4,052,403
[45] Oct. 4, 1977

[54] 2-HYDROXYIMINO-1,2,3,4,6,7-HEXAHYDRO-11BH-BENZO [A] QUINOLISINE DERIVATIVES

[75] Inventors: Csaba Szantay; Andras Vedres; Karoly Thuranszky; Gyula Balogh; Maria Vedres nee Kozma, all of Budapest, Hungary

[73] Assignee: EGYT Gyogyszervegyeszeti Gyar, Budapest, Hungary

[21] Appl. No.: 678,902

[22] Filed: Apr. 21, 1976

[30] Foreign Application Priority Data

Apr. 21, 1975 Hungary .............................. EE 2321

[51] Int. Cl.$^2$ .......................................... C07D 215/42
[52] U.S. Cl. .............................................. 260/288 CF
[58] Field of Search ................................... 260/288 CF

[56] References Cited
U.S. PATENT DOCUMENTS 3,830,818  8/1974  Hackmack et al. ........... 260/288 CF Primary Examiner—R. Gallagher

[57] ABSTRACT

Novel 2-hydroxyimino-1,2,3,4,6,7-hexahydro-11bH-benzo [a] quinolisine derivatives are prepared by reacting substituted 2-oxo-benzo[a]quinolisine compounds with hydroxylamine or an acid addition salt thereof. The described compounds and their acid addition salts and quaternary onium derivatives evidence psychopharmacological properties in the absence of adverse side effects.

6 Claims, No Drawings

2-HYDROXYIMINO-1,2,3,4,6,7-HEXAHYDRO-11BH-BENZO [A] QUINOLISINE DERIVATIVES

This invention relates to benzo[a]quinolisine derivatives and to a method for their preparation. More particularly, the present invention relates to 2-hydroxyimino-1,2,3,4,6,7-hexahydro-11bH-benzo[a]quinolisine derivatives and the preparation thereof.

Although compounds having a benzo[a] quinolisine structure have been described in the literature (See Belgian Pat. No. 642,060 and Journal of Organic Chemistry, Volume 31, Page 797, 1966), 2-hydroxyimino-1,2,3,4,6,7-hexahydro-11-bH-benzo[a]quinolisine derivatives have not been known heretofore.

In accordance with the present invention, a technique is described for the preparation of biologically active novel 2-hydroxyimino-1,2,3,4,6,7-hexahydro-11bH-benzo[a]quinolisine derivatives of the general formula

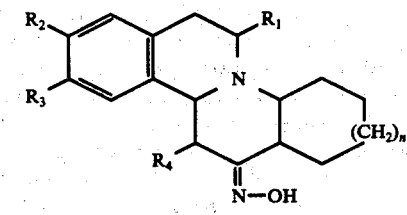

(I)

wherein $R_1$ and $R_4$ are each selected from the group consisting of hydrogen and an alkyl group of 1-4 carbon atoms, $R_2$ and $R_3$ are each selected from the group consisting of hydrogen, a hydroxyl group, an alkoxy group of from 1-4 carbon atoms and an $R_2$-$R_3$ joint methylenedioxy group, and $n$ is an integer from 1-2. The invention also contemplates the acid addition salts, the quaternary onium derivatives and pharmaceutical compositions containing the foregoing compounds.

The novel compounds herein described may conveniently be prepared in accordance with the invention by reacting a 2-oxo-benzo[a]quinolisine derivative of the general formula

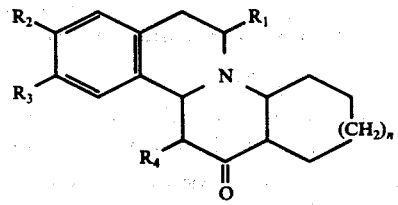

(II)

wherein $R_1$, $R_2$, $R_3$, $R_4$ and $n$ are as set forth above, with hydroxylamine or an acid addition salt thereof. Following, the resultant quinolisine derivative may be converted to the corresponding salt thereof by reaction with organic or inorganic acids, or by quaternization of the nitrogen atom.

The preparative reaction with hydroxylamine is preferably conducted in an aqueous or alcoholic medium. Other solvents may also be employed for the oxime formation, the only constraint being that no reaction should occur between solvent and reactant. Studies have revealed that the most convenient procedure for introducing the hydroxylamine is by way of its hydrochloride, the hydroxylamine being liberated from its acid addition salt directly into the reaction medium. It may also be noted that the 2-oxo-benzo[a]quinolisine derivatives reacted with hydroxylamine may themselves be prepared by reacting a correspondingly substituted 3,4-dihydroisoquinolisine with an appropriate acylcycloalkene.

The acid addition salts of the novel compounds herein described may conveniently be prepared by using an acid addition salt of hydroxylamine as a reactant or by reaction of the free base of the desired compound with an organic or inorganic acid. Similarly, the quaternary onium derivatives of the desired compounds may be obtained by reacting the free bases with alkylating agents, methyl iodide being particularly well-suited for this purpose.

In principle, compounds of the general formula (I), above, wherein $R_1$ and $R_4$ represent hydrogen, contain three chiral carbon atoms (the carbon atoms in positions 3, 4 and 11b) and, consequently, the formation of four diastereomers is anticipated, such diastereomers being designated "a", "b", "c", and "d". Experimentation has shown that the use of a reactant of the general formula (II), above, is in the form of a diastereomeric mixture, the product will also be a mixture of diastereomers. Similarly, when the pure "a", "b", "c", or "d" isomer of compound (II) is employed as a reactant, the resultant product is the corresponding isomer.

Oxime formation as described herein may also be coupled with epimerization, as for example, by reacting a 2-oxo-benzo [a]quinolisine of the general formula (II) with hydroxylamine in the presence of a basic catalyst. The reaction of diastereomer "b" of 2-oxo-benzo[a]quinolisine with hydroxylamine in the presence of sodium hydroxide yields the 2-hydroxyimino-benzo [a]quinolisine end product in the form of a mixture of diastereomers "b"and "c". In the event acid catalysts are employed, epimerization occurs only to a limited extent, if at all.

The diastereomers of compounds (I), above, may readily be separated, each from the other, by conventional thin layer chromatography. A typical procedure involves the use of (a) an adsorbent such as Kieselgel $GF_{254}$, a well-knwon commerically available adsorbent containing 10 percent boric acid, (b) an eluent such as a 9:1 mixture of chloroform and methanol and (c) iodine vapor or ultraviolet light as the developer. It has usually been found that the highest retention factors of compounds of formula (I) occur in the diastereomer "a", retention factors of the other isomers decreasing the sequence "b," "c" and "d." Other separation procedures such as fractional crystallization, salt formation and subsequent fractional crystallization, selective extraction and the like may also be used.

Conventional analytical means well-known to those skilled in the art may be used for identification of the isomers, namely, the IR and NMR spectra. Thus, for example, in the IR spectra of "a" isomers, intense Bohlmann bands are evidenced in marked conrast with the "b" and "c" isomers. Similarly, the proton in position 11b evidences a characteristic signal in the NMR spectra, such being a quartet for the "a" and "b" isomers and a triplet for isomer "c".

Resolution of the individual diastereomers is effected with optically active camphor-10-sulfonic acid. However, when the reactant designated (II) is optically active, the resultant product is also optically active.

It will be appreciated by those skilled in the art that all of the stereoisomers, optical isomers and isomeric mixtures of compounds of the general formula (I) are within the scope of the present invention.

The novel compounds described herein have been found to evidence psychosedative effects. This conclusion was based upon experimentation with mice by measuring their inhibition ability exerted on amphetamine-provoked hypermotility. the animals so tested were treated subcutaneously with 3 mg/kg of amphetamine (α-methyl-phenethylamine) while simultaneously administering the novel compound of formula (I) herein. A control test was run in which no psychosedative agent was used. The extent of hypermotility observed in the control group treated only with 3 mg/kg of amphetamine was regarded as 100%, and the percentage of inhibition observed in the test groups was related to this value. The results are set forth in Table I below.

TABLE 1

| Compound | Dosage mg/kg s.c. | Inhibition, % |
| --- | --- | --- |
| 2-Hydroxyimino-3,4-cyclohexano-9,10-dimethoxy-1,2,3,4,6,7-hexahydro-11bH-benzo[a]quinolisine (isomer "b") | 20 | 66 |
| 2-Hydroxyimino-3,4-cyclohexano-9,10-dimethoxy-1,2,3,4,6,7-hexahydro-11bH-benzo[a]quinolisine (isomer "a") | 100 | 33 |
| 2-Hydroxyimino-3,4-cyclopentano-9,10-dimethoxy-1,2,3,4,6,7-hexahydro-11bH-benzo[a]quinolisine (isomer "b") | 100 | 40 |
| 2-Hydroxyimino-3,4-cyclopentano-9,10-dimethoxy-1,2,3,4,6,7-hexahydro-11bH-benzo[a]quinolisine (isomer "a") | 100 | 61 |
| 2-Hydroxyimino-3,4-cyclohexano-9,10-diethoxy-1,2,3,4,6,7-hexahydro-11bH-benzo[a]quinolisine (isomer "b") | 100 | 85 |
| 2-Hydroxyimino-3,4-cyclohexano-9,10-dimethoxy-1,2,3,4,6,7-hexahydro-11bH-benzo[a]quinolisine (isomer "c") | 100 | 33 |

The acute toxicities of the new compounds having the general formula (I) were measured on mice, under subcutaneous administration. The $LD_{50}$ values are listed in Table 2.

TABLE 2

| Compound | $LD_{50}$ mg/kg s.c. |
| --- | --- |
| 2-Hydroxyimino-3,4-cyclohexano-9,10-dimethoxy-1,2,3,4,6,7-hexahydro-11bH-benzo[a]quinolisine (isomer "b") | >500 |
| 2-Hydroxyimino-3,4-cyclohexano-9,10-dimethoxy-1,2,3,4,6,7-hexahydro-11bH-benzo[a]quinolisine (isomer "a") | >500 |
| 2-Hydroxyimino-3,4-cyclopentano-9,10-dimethoxy-1,2,3,4,6,7-hexahydro-11bH-benzo[a]quinolisine (isomer "b") | >500 |
| 2-Hydroxyimino-3,4-cyclopentano-9,10-dimethoxy-1,2,3,4,6,7-hexahydro-11bH-benzo[a]quinolisine (isomer "a") | >500 |
| 2-Hydroxyimino-3,4-cyclohexano-9,10-diethoxy-1,2,3,4,6,7-hexahydro-11bH-benzo[a]quinolisine (isomer "b") | >300 |
| 2-Hydroxyimino-3,4-cyclohexano-9,10-dimethoxy-1,2,3,4,6,7-hexahydro-11bH-benzo[a]quinolisine (isomer "c") | >200 |

From the foregoing experimentation, it was observed that diastereomer "b" of 2-hydroxyimino-3,4-cyclohexano-9,10-dimethoxy-1,2,3,4,6,7-hexahydro-11bH-benzo[a]quinolisine was a highly effective composition. Experimentation with this compound on waking cats and dogs provoked symptons similar to those os scopolamine. Accordingly, the effects of this "b" iosmer were compared directly with scopolamine by the use of a subcutaneous dosage of 100 mg/kg of the former and 150 mg/kg of the latter. In the case of cats, the active agents first caused restlessness coupled with hallucinations of the same type and degree, and 30 minutes after administration of the agents, all animals were paralyzed. However, the compound of the present invention provoked a more complete akinesia than scopolamine. Scopolamine-treated animals remained in a standing position whereas animals treated in accordance with the invention could not be brought to a standing position, their limbs immediately sliding apart although the carriage of their heads remained stationary. Upon administering painful stimuli, the animals gave a strong mewing response, and a long-lasting blepharospasm and mewing was attained by dropping capsaicine, N-(4-hydroxy-3-methoxybenzyl)-(8-methyl-6-nonenamide) into their eyes.

There were also other differences between the two compositions. Specifically, scopolamine did not exert anticholinerg activity but did evidence a marked atropine-like effect. Still another distinction resides in the fact that the compound described above, the "b" isomer, did not potentiate the analgesic effect of morphine nor did it potentiate the narcosis provoked by hexobarbital (5-(1-cyclohexaanyl)-1,5-dimethylbarbituric acid).

When the said "b" isomer was administered to waking dogs in a subcutaneous dosage of 10 mg/kg it provoked remarkable quietness and the animals fell asleep. This was not a narcotic effect, for the dogs were awakened readily upon smell stimuli related to food or slight noice and tactile stimuli. The animals evidenced normal behavior after awakening. Scopolamine is known to exert a similar effect on dogs in small dosages.

It is, of course, well-known that scopolamine is widely used in psychotherapy and that it possesses therapeutic psychosedative effects when administered in small dosages. However, its strong atropine-like parasympatholytic side effects. Diastereomer "b" of 2-hydroxyimino-3,4-cyclohexano-9,10-diethoxy-1,2,3,4,6,7-hexahydro-11-bH-benzo[a]quinolisine evidences similar effects on cats when administered in a subcutaneous dosage of 100 mg/kg.

Several examples of the present invention are set forth below. It will be appreciated by those skilled in the art that the examples are merely for purposes of exposition and are not to be construed as limiting.

EXAMPLE 1

1-Methyl-2-oxo-3,4-cyclopentano-9,10-dimethoxy-1,2,3,4,6,7-hexahydro-11bH-benzo[a]quinolisine a. A mixture of 11.4 g (0.05 moles) of 6,7-dimethoxy-3,4-dihydroisoquinoline hydrochloride, 19 ml of 1-propionylcyclopentane, 20 ml of ethanol and 1 ml of water was refluxed for 30 hours. The mixture was concentrated, the residue acidified with 1 ml of 1 N hydrochloric acid, and the acidic residue taken up in 200 ml of water. Then, the aqueous mixture was washed three times with 20 ml of water. Then, the aqueous mixture was washed three times with 20 ml of benzene, and then its pH adjusted to 9 by adding saturated aqueous sodium carbonate solution. The separated oil was extracted three times with 30 ml of benzene. Next, the benzene solutions were combined, dried and evaporated. The residue, weighting 12.5 g (80%) was dissolved in 100 ml of benzene, and the solution extracted five times with 0.6 N hydrochloric acid total of 100 ml of hydrochloric acid was required). The third extract contained mainly diastereomer "c", whereas the fourth and fifth extracts contained diastereomer "a". The third extract was rendered alkaline (pH = 9). The separated oil was dissolved in 50 ml of benzene and this solution extracted in ten portions with a mixture of 4 ml of 6 N hydrochloric acid and 100 ml of water. The third and fourth extracts were combined and rendered alkaline (pH = 9). The separated oil was extracted into benzene and the solution evaporated. The oily residue was then triturated with ether and the resulting crystals filtered off. The obtained crude product, weighing 0.5 g, was recrystallized from ether. 0.25 g of pure diastereomer "c" were obtained; m.p.: 142°–146° C.

The fourth and fifth acidic fractions obtained as described above were combined and rendered alkaline (pH = 9). The separated oil was dissolved in 50 ml of benzene, and the benzene solution extracted in ten portions with a mixture of 100 ml of water and 2 ml of 6 N hydrochloric acid. From the first and second fractions diastereomer "c" was separated, whereas fractions 6 to 9 contained diastereomer "a". These fractions were combined with fractions 7 to 9 obtained in the second acid extraction step of the separation of diastereomer "c", the solution rendered alkaline (pH = 9), and the alkaline mixture extracted with benzene. The benzene solution was then dried and evaporated. The obtained residue, weighing 2 g, was dissolved in a 2"l mixture of ether and ethanol, and the solution acidified to pH = 2 with dry perchloric acid. The resulting 1.8 g of white, crystalline substance was recrystallized from a mixture of 10 ml of water and 5 ml of ethanol. 0.8 g of the perchlorate salt were obtained; m.p.: 192–200° C. This salt was dissolved in aqueous ethanol and the solution rendered alkaline (pH = 9). The resulting crude, crystalline base, weighing 0.6 g, was recrystallized from a mixture of 6 ml of ethanol and 10 ml of water. 0.45 g of pure diastereomer "a" were obtained; m.p.: 109°–112° C.

b. A mixture of 9.5 g (0.05 moles) of 6,7-dimethoxy-3,4-dihydroisoquinoline, 19 ml of 1-propionyl-cyclopentane, 20 ml of ethanol, 2 ml of 10% aqueous sodium hydroxide solution and 3 ml of water was refluxed for 16 hours. The mixture was evaporated in vacuo and the residue taken up in 100 ml. of ether. The etheral solution was washed three times with 50 ml of water and extracted in ten portions with a mixture of 10 ml of 6 N hydrochloric acid and 90 ml of water. Diastereomer "b" accumulated in fractions 4 to 10. These fractions were combined and rendered alkaline (pH = 9). The separated crystals were filtered off. 6.2 g (39%) of crude diastereomer "b" were obtained; m.p.: 109°–117° C. The crude product was recrystallized thrice from fourfold amounts of ethanol. 0.7 g (4%) of pure diastereomer "b" were obtained; m.p.: 126°–138° C.

EXAMPLE 2

2-Hydroxyimino-3,4-cyclohexano-1,2,3,4,6,7-hexahydro-11bH-benzo[a]quinolisine 0.5 g (1.96 moles) of "a"-2-oxo-3,4-cyclohexano-1,2,3,4,6,7-hexahydro-11bH-benzo[a]quinolisine, a compound prepared according to the process described in Example 1, were added at 90° to 100° C to a stirred solution of 1.0 g of hydroxylamine hydrochloride in 9.4 ml of water. The mixture was stirred at the same temperature for 10 minutes and then cooled to room temperature. The separated crystals were filtered off, washed with water and dried. 0.45 g (70%) of the hydrochloride salt were obtained; m.p.: 143°–145° C. This salt was dissolved in 20 ml of 50% ethanol under heating, and the solution rendered alkaline (pH = 8). The separated precipitate was filtered off, washed with water, and dried. The resulting 0.40 g of the crude base were recrystallized from 30 ml of chloroform. 0.30 g (56%) of pure diastereomer "a" were obtained; m.p.: 138°–140° C.

Analysis:
calculated for $C_{17}H_{22}ON_2$ (M = 270.36):
C: 75.52%, H: 8.20%, N: 10.36%;
found: C: 73.44%, H: 8.75%, N: 9.61%.

IR-spectrum (taken in a pellet containing 4 mg of the compound to be analyzed and 400 mg of KBr):
hydroxy group: 3420, 3170, 3070 (diffuse) cm$^{-1}$,
imino group: 1660 cm$^{-1}$,
aromatic skeletal vibration: 1570, 1500 cm$^{-1}$.

NMR-spectrum (taken in a 10% deuterochloroform solution using tetramethylsilane as internal standard):
$\delta$ = 10.63 (hydroxyimino proton in position 2), 6.95 (protons in positions 8 and 11) ppm.

EXAMPLE 3

2-Hydroxyimino-3,4-cyclopentano-1,2,3,4,6,7-hexahydro-11bH-benzo[a]quinolisine 0.5 g (2.38 moles) of "a"-2-oxo-3,4-cyclopentano-1,2,3,4,6,7-hexahydro-11bH-benzo[a]quinolisine, a compound prepared according to the process described in Example 1, were added at 90° to 100° C to a stirred solution of 1.0 g of hydroxylamine hydrochloride in 9.4 ml of water. The mixture was stirred at the same temperature for 10 minutes and then cooled to room temperature. The separated crystals were filtered off, washed with water and dried. 0.45 g (74%) of the hydrochloride salt were obtained; m.p.: 224°–226° C. The melting point did not change after a recrystallization from 20-fold amount of 98% ethanol.

0.3 g of the above salt were dissolved in 6 ml of 50% ethanol and the solution rendered alkaline with 0.4 ml of saturated aqueous sodium carbonate solution. The separated precipitate was filtered off, washed with water and dried. 0.25 g of crude product were obtained; m.p.: 168°–172° C. After recrystallization from 6 ml of ethanol, 0.20 g of pure diastereomer "a" were obtained; m.p.: 163°–165° C.

IR-spectrum:
hydroxy group: 3180, 3070 (diffuse) cm$^{-1}$,
imino group: 1660 cm$^{-1}$,
aromatic skeletal vibration: 1580, 1495 cm$^{-1}$.

EXAMPLE 4

(−)-2-oxo-3,4-cyclopentano-6-methyl-1,2,3,4,6,7-hexahydro-11bH-benzo[a]quinolisine A mixture of 14.5 g (0.1 mole) of (−)-3-methyl-3,4-dihydroisoquinoline, 25 ml of 1-acetyl-cyclopentene, 0.67 g of methylamine hydrochloride and 75 ml of ethanol was maintained at 75° C for 8 hours. The reaction mixture was kept in a refrigerator overnight and then the separated crystals were filtered off and washed with ethanol. The resulting 6.6 g (26%) of crude, optically active isomer "a" (m.p.: 101°–104° C) were recrystallized from 8-fold amount of methanol. The crystals were filtered off at 0° C. 4.0 g (16%) of pure, optically active isomer "a" were obtained; m.p.: 102°–104° C.

EXAMPLE 5

(−)-6-Methyl-2-hydroxyimino-3,4-cyclopentano-1,2,3,4,6,7-hexahydro-11bH-benzo[a]quinolisine hydrochloride 2.1 g of hydroxylamine hydrochloride were dissolved in 50 ml of ethanol under heating, and then 2.55 g (0.01 mole) of (−)-2-oxo-3,4-cyclopentano-1,2,3,4,6,7-hexahydro-11bH-benzo [a]quinolisine (isomer "a", prepared as described in Example 4) were added to the solution. The mixture was refluxed for 15 minutes and then cooled. The separated crystalline substance was filtered off and washed with ethanol. 2.85 g (93%) of the crude hydrochloride salt was obtained; m.p.: 198°–206° C (decomposition). This crude substance was recrystallized twice from ethanol. 1.0 g (34%) of the title compound (isomer "a") were obtained; m.p.: 196°–200° C (decomposition). $(\alpha)_D^{20} = -149°$ (c = 1% in methanol).

Analysis:
calculated for $C_{17}H_{23}N_2OCl \cdot H_2O$:
 C: 64.32%; H: 8.82%, Cl: 10.92%;
found: C: 64.35%, H: 8.78%, Cl: 10.74%.
IR-spectrum:
hydroxy group: 3240 (diffuse) cm$^{-1}$,
quaternary nitrogen atom: 2560 (diffuse) cm$^{-1}$,
imino group: 1680 cm$^{-1}$,
aromatic skeletal vibration: 1455, 1500 cm$^{-1}$.
UV-spectrum: $\lambda_{max.}^{EtOH} = 264$ nm ($\epsilon = 296$).

EXAMPLE 6

1-Methyl-2-hydroxyimino-3,4-cyclopentano-9.10-dimethoxy-1,2,3,4,6,7-hexahydro-11bH-benzo[a]quinolisine 0.4 g (1.27 moles) of "a"-1-methyl-2-oxo-3,4-cyclopentano-9,10-dimethoxy-1,2,3,4,6,7-hexahydro-11bH-benzo[a]quinolisine, prepared as described in Example 1, were added at 90° to 100° C to a stirred solution of 0.8 g of hydroxylamine hydrochloride in 7.5 ml of water. The mixture was stirred at the same temperature for an additional 30 minutes and then cooled to room temperature. The separated crystalline substance was filtered off, washed with water, and dried. 0.1 g of the hydrochloride salt was obtained; m.p.: 203°–207° C. The filtrate was rendered alkaline (pH = 8), the separated precipitate filtered off, washed with water, and dried. 0.1 g of the free base was obtained; m.p.: 200°–203° C. The mother liquor was allowed to stand for one day and then the separated additional 0.2 g of free base were filtered off. This latter fraction melted at 199°–203° C. The two fractions (0.3 g, 72%) were combined and recrystallized from a mixture of 20 ml of ethanol and 2 drops of water. 0.15 g (36%) of pure diastereomer "a" were obtained; m.p.: 206°–209° C.

Analysis:
calculated for $C_{19}H_{26}N_2O_3$ (M = 330.41):
 C: 69.06%, H: 7.93%, N: 8.48%;
found: C: 69.01%, H: 8.32%, N: 8.19%.
IR-spectrum:
hydroxy group: 3470 cm$^{-1}$,
imino group: 1630 (very weak) cm$^{-1}$,
aromatic skeletal vibration: 1610, 1520 cm$^{-1}$,
Bohlmann-bands: 2820, 2760 cm$^{-1}$.
UV-spectrum: $\lambda_{max.} = 282$–286 nm ($\epsilon = 3900$).

EXAMPLE 7

2-Hydroxyimino-3,4-cyclopentano-9-methoxy-10-hydroxy-1,2,3,4,6,7,-hexahydro-11-bH-benzo[a]quinolisine hydrochloride 1.4 g (0.005 mole) of 2-oxo-3,4-cyclopentano-9-methoxy-10-hydroxy-1,2,3,4,6,7-hexahydro-11bH-benzo[a]quinolisine (diastereomer "a", a compound obtained according to the process described in Example 1) were dissolved in 70 ml of ethanol with heating, and a solution of 1.05 g of hydroxylamine hydrochloride in 25 ml of ethanol was added. The mixture was boiled for 5 minutes and then evaporated to one-third of its initial volume. The crystals which separated upon cooling were filtered off, washed with ethanol and dried. 1.50 g (88$) of the crude hydrochloride was obtained. After recrystallization from 44 ml of methanol, 0.90 g (53%) of pure diastereomer "a"-hydrochoride was obtained; m.p.: 187°–197° C.

Analysis:
calculated for $C_{17}H_{23}N_2O_3Cl$ (M = 338.83):
 C: 60.27%, H: 6.84%, N: 8.27%, Cl: 10.46%;
found: C: 57.43%, H: 7.79%, N: 8.16%, Cl: 9.47%.
IR-spectrum:
hydroxy group: 3460, 3390 (diffuse) cm$^{-1}$,
quaternary nitrogen atom: 2570 cm$^{-1}$,
aromatic skeletal vibration: 1620, 1540 (broad) cm$^{-1}$.

EXAMPLE 8

2-Hydroxyimino-3,4-cyclohexano-9,10-methylenedioxy-1,2,3,4,6,7-hexahydro-11bH-benzo[a]quinolisine 3.14 g (0.015 mole) of "b"-2-oxo-3,4-cyclohexano-9.10-methylenedioxy-1,2,3,4,6,7-hexahydro-benzo[a]-quinolisine, a compound prepared according to the process described in Example 1, was dissolved in a mixture of 60 ml of ethanol and 30 ml of chloroform with heating. A solution of 1 g of sodium hydroxide in 15 ml of water was added to the mixture, followed by a solution of 0.75 g of hydroxylamine hydrochloride in 1 ml of water. The resulting mixture was stirred and refluxed for 2 hours. Thereafter, 0.5 g of hydroxylamine hydrochloride was added, and the mixture allowed to stand overnight. The reaction mixture was evaporated. Then, the residue was triturated with 10 ml of ater, the separated solid filtered off, washed several times with water, and dried. 2.9 g (88%) of crude diastereomer "b" was obtained; m.p.: 206°–215° C. After recrystallization from 30-fold amount of chloroform, the product melted at 233°–239° C.

Analysis:
calculated for $C_{18}H_{22}N_2O_3$ (M = 314.39):
 C: 68.77%, H: 7.05%, N: 8.91%;
found: C: 68.72%, H: 6.99%, N: 8.78%.
IR-spectrum:
hydroxy group: 3250, 3120 (diffuse) cm$^{-1}$,
imino group: 1650, 1620 cm$^{-1}$,
aromatic skeletal vibration: 1500, 1470 cm$^{-1}$.
NMR-spectrum: $\delta$ = 8.50 (diffuse; 2-N-O$\underline{H}$), 6.67 and 6.50 (protons in positions 8 and 11), 5.82 (9,10-O-C$\underline{H}_2$-O) ppm.

EXAMPLE 9

2-Hydroxyimino-3,4-cyclopentano-9,10-dimethoxy-1,2,3,4,6,7-hexahydro-11bH-benzo[a]quinolisine 9.9 g (0.03 mole) of "a"-2-oxo-3,4-cyclopentano-9,10-dimethoxy-1,2,3,4,6,7-hexahydro-11bH-benzo[a]- quinolisine, a compound prepared according to the process described in Example 1, was dissolved in 150 ml of ethanol with heating. A solution of 2.3 g of hydroxylamine hydrochloride in 6 ml of water was added, and the mixture rendered alkaline with a solution of 1.4 g of sodium hydroxide in 6 ml of water. The reaction mixture was refluxed for 10 minutes and then allowed to stand in a refrigerator overnight. The separated crystals were filtered off and washed with cold ethanol. 9.3 g (90%) of crude diastereomer "a" was obtained; m.p.: 184°-204° C. After two recrystallizations from a 3:1 mixture of tetrahydrofuran and ethanol, 4.25 g of pure diastereomer "a" were obtained; m.p.: 201°-203° C.

Analysis:
calculated for $C_{20}H_{28}N_2O_3$ (M = 344.46):
 C: 69.74%, H: 8.19%, N: 8.13%;
found: C: 68.85%, H: 8.52%, N: 8.60%.
IR-spectrum:
hydroxy group: 3290 cm$^{-1}$,
aromatic skeletal vibration: 1620, 1525 cm$^{-1}$.
 NMR-spectrum: $\epsilon$ = 9.78 (singlet, 2N-O$\underline{H}$), 6.72, 6.56 (singlets, protons in positions 8 and 11), 3.88, 3.86 (singlets, 9, 10-OC$\underline{H}_3$) ppm.

EXAMPLE 10

2-Oxo-3,4-cyclohexano-9,10-dimethoxy-1,2,3,4,6,7-hexahydro-11bH-benzo[a]quinolisine A mixture of 192 g (1 mole) of 6,7-dimethoxy-3,4-dihydroisoquinoline, 250 ml of 1-acetyl-cyclohexene, 500 ml of ethanol and 40 ml of 0.1% aqueous sodium hydroxide solution was refluxed under a nitrogen atmosphere for 55 hours. During this period, about 50% of the dihydroisoquinoline compound transformed. The reaction mixture was maintained in a refrigerator overnight. Thereafter, the separated crystals were filtered off and washed twice with 100 ml of ethanol. 93 g (30%) of a substance melting at 149°-152° C were obtained; this substance was diastereomer "b" containing about 5 to 10% of diastereomer "a" as impurity. After recrystallization from tenfold amount of ethanol, 73 g (23%) of pure diastereomer "b" were obtained; m.p.: 153°-154° C.

6.7 g (0.1 mole) of methylamine hydrochloride were added to the mother liquor separated after the cycloaddition step and the mixture refluxed for 4 hours. During this period, the remainder of the isoquinoline compound transformed. The reaction mixture was maintained in a refrigerator overnight. Thereafter, the separated crystals were filtered off and washed twice with 100 ml of ethanol. 109 g (35%) of a substance melting at 146°-149° C were obtained; this substance was diastereomer "a" containing about 10 to 15% of diastereomer "b" as impurity. After recrystallization from fivefold amount of benzene, 57 g (18%) of pure diastereomer "a" was obtained; m.p.: 155°-157° C.

The mother liquor obtained in this recrystallization step was maintained in a refrigerator overnight. The separated crystals were filtered off and washed twice with 50 ml of ethanol. 38 g (12%) of a crystalline substance melting at 140°-144° C were obtained. This substance was an 8:2 mixture of the "a" and "b" diastereomers.

The mother liquor was evaporated and the residue dissolved in 200 ml of benzene. The benzene solution was extracted five times with 100 ml of 2% aqueous hydrochloric acid. The acidic solutions were combined and rendered alkaline (pH = 8) with saturated aqueous sodium carbonate solution. The separated oil was extracted four times into 100 ml of benzene. The benzene solutions were combined, washed four times with 100 ml of water, dried over calcined sodium sulfate, filtered and evaporated. 55 g (18%) of a solid residue were obtained. This residue contained 50% of diastereomer "a" and 35% of diastereomer "b".

The total yield of the above process is 95%.
Analysis:
Calculated for $C_{19}H_{25}NO_3$ (M = 315.42):
 C: 72.35%, H: 7.99%, N: 4.44%;
found: C: 72.44%, H: 8.11%, N: 4.52%; (isomer "a")
 C: 72.22%, H: 8.13%, N: 4.46%, (isomer "b").
UV-spectrum:
 isomer "a": $\lambda_{max}$ = 283 nm (log $\epsilon$ = 3.602)
 isomer "b": $\lambda_{max}$ = 283 nm (log $\epsilon$ = 3.602).
IR-spectrum: (cm$^{-1}$)

|  |  | isomer "a" | isomer "b" |
|---|---|---|---|
| oxo group |  | 1705 | 1710 |
| aromatic skeletal vibration |  | 1520 1615 | 1525 1615 |
| Bohlmann band |  | 2765 2820 (weak) | — |
| —O—CH$_3$ | symmetric stretching | 2845 | 2845 |
| —CH$_2$— | symmetric stretching | 2865 | 2865 |
| —CH$_2$— | asymmetric stretching | 2945 | 2945 |
| —OCH$_3$ | asymmetric stretching | 2980 | 2980 |
| NMR-spectrum ($\delta$ values): |  | isomer "a" | isomer "a" |
| 9,10-OCH$_3$ |  | 3.83 (singlet) | 3.85 (singlet) |
| 11b-H |  |  | 4.22 (quartet, J = 10.5) |
| 8-H, 11-H |  | 6.62, 6.55 | 6.58, 6.53. |

EXAMPLE 11

2-Hydroxyimino-3,4-cyclohexano-9,10-dimethoxy-1,2,3,4,6,7-hexahydro-11bH-benzo[a]quinolisine a. 18.4 g (0.0585 mole) of "a"-2-oxo-3,4-cyclohexano-9,10-dimethoxy-1,2,3,4,6,7-hexahydro-11bH-benzo[a]quinolisine, a compound obtained according to the process described in Example 1, were dissolved in 185 ml of ethanol with heating. A solution of 4.1 g of hydroxylamine hydrochloride in 30 ml of water was added, and the mixture rendered alkaline by adding a solution of 2.6 g of sodium hydroxide in 4 ml of water. The mixture was refluxed for 5 minutes and then maintained in a refrigerator overnight. The separated crystals were filtered off, washed three times with 15 ml of 50% ethanol and dried. 15.2 g (79%) of a crystalline substance melting at 237°-242° C were obtained. This substance was recrystallized from 1200 ml of ethanol to obtain 10.5 g (55%) of diastereomer "a"; m.p.: 238°-241° C.

The hydrogen maleate of this compound was prepared as follows: 5 g of maleic acid were dissolved in 30 ml of ethanol, the solution heated to 40°-50° C, and 10g of diastereomer "a" added. The separated crystals were filtered off, washed with ethanol and dried. 12 g (89%) of diastereomer "a"-hydrogen maleate were obtained; m.p.: 171°-172° C. The melting point did not change after recrystallization from 3.5-fold amount of ethanol.

b. 31.5 g (0.1 mole) of "b"-2-oxo-3,4-cyclohexano-9,10-dimethoxy-1,2,3,4,6,7-hexahydro-11bH-benzo[a]quinolisine, a compound obtained as described in Example 10, were added at 95° C to a stirred solution of 31.5 g of hydroxylamine hydrochloride in 315 ml of water. The mixture was refluxed for 5 minutes and then cooled to 8° C. The separated crystals were filtered off, washed three times with 20 ml of 50% ethanol, and the resultant 35.7 g (98%) of hydrochloride salt, melting at 213°–217° C dissolved in 800 ml of 50% ethanol with heating. A solution of 4.4 g of sodium hydroxide in 20 ml of water was added to the hot mixture. The reaction mixture was cooled to room temperature, the separated substance filtered off, washed with 50% ethanol and dried. 25.2 g (77%) of crude diastereomer "b" were obtained; m.p.: 216°–218° C. After recrystallization from 100-fold amount of ethanol, the product melted at 217°–219° C.

The hydrogen maleate of the above compound was prepared as follows: one part of maleic acid was dissolved in tenfold amount of ethanol and two parts of diastereomer "b" were added to the solution. Thereafter, ether was added in portions until the mixture became cloudy, and the cloudy mixture allowed to stand in a refrigerator overnight. The separated crystals were filtered off and washed with a 1:2 mixture of ether and ethanol. The crude salt, melting at 175°–178° C, was obtained with a yield of 91%. After recrystallization from tenfold amount of 98% ethanol, the product melted at 177°–179° C.

c. 31.5 g (0.1 mole) of "b"-2-oxo-3,4-cyclohexano-9,10-dimethoxy-1,2,3,4,6,7-hexahydro-11bH-benzo[a]quinolisine, a compound obtained as described in Example 10, were dissolved in 300 ml of ethanol with heating. A solution of 10g of sodium hydroxide in 150 ml of water was added, followed by the addition of a solution of 7.5 g of hydroxylamine hydrochloride in 10 ml of water. The reaction mixture was refluxed for 10 minutes, allowed to cool to room temperature, and the separated substance filtered off. 25.1 g (78%) of a solid melting at 187°–190° C were obtained. This substance was a mixture of diastereomers "b" and "c". The mother liquor was evaporated, the solid residue triturated with water, and the crystalline substances filtered off. Further 5.45 g (16%) of an isomeric mixture were obtained; m.p.: 184°–189° C. 15g of maleic acid were dissolved in 200 ml of 98% ethanol, and the resultant 30.55 g of crude isomeric mixture added to this solution. The hot solution was allowed to cool to room temperature. The separated crystals were filtered off and washed with cold ethanol. The resulting 8.1 g (17%) of crystalline substance consisted mainly of diastereomer "c" and melted at 189°–193° C. After recrystallization from 100 ml of 94% ethanol, 3.7 g of pure diastereomer "c"-hydrogen maleate were obtained; m.p.: 194°–196° C. The mother liquors contained the mixture of the two diastereomers.

The base was liberated as follows: 2 g of the hydrogen maleate were dissolved in 20 ml of 50% ethanol and the solution rendered alkaline by adding 4 ml of 10% aqueous sodium hydroxide solution. The separated substance was filtered off, washed with distilled water and dried. 1.4 g of pure diastereomer "c" were obtained; m.p.: 218°–223° C.

Analysis:
calculated for $C_{19}H_{26}N_2O_3$ (M = 330.40):
C: 69.06%, H: 7.93%, N: 8.48%;
found: C: 69.25%, H: 8.13%, N: 9.13% (isomer "a")
C: 69.95%, H: 8.12%, N: 8.52% (isomer "b")
C: 68.26%, H: 8.30%, N: 8.73% (isomer "c").
IR-spectrum (cm$^{-1}$):

| | isomer "a" | isomer "b" | isomer "c" |
|---|---|---|---|
| hydroxy group | 3250,3160 (diffuse) | 3090,3200 (diffuse) | 3480,3090 (diffuse) |
| imino group | 1675 (very weak) | 1670 (very weak) | 1670 (very weak) |
| aromatic skeletal vibration | 1620,1525 | 1620,1530 | 1615, 1525 |
| Bohlmann-bands | 2760,2820 (very weak) | — | — |
| NMR-spectrum ($\delta$ values): | isomer "a" | isomer "b" | isomer "c" |
| 2-N-OH | 9.90 (singlet) | 9.37 (singlet) | 10.25 (singlet) |
| 9,10-OCH$_3$ | 3.84,3.86 (singlets) | 3.84,3.85 (singlets) | 3.60,3.20 (singlets) |
| 11b-H | — | — | 4.23 (triplet) |
| 8-H, 11-H | 6.60,6.71 (singlets) | 6.58,6.70 (singlets) | 6.53,6.80 (singlets) |

EXAMPLE 12

2-Hydroxyimino-3,4-cyclopentano-9,10-dimethoxy-1,2,3,4,6,7-hexahydro-11bH-benzo[a]quinolisine a. 10 g of "a"-2-oxo-3,4-cyclopentano-9,10-dimethoxy-1,2,3,4,6,7-hexahydro-11bH-benzo[a]quinolisine, a compound obtained according to the process described in Example 1, were dissolved in 35 ml of ethanol with heating. A solution of 2.5 g (0.035 mole) of hydroxylamine hydrochloride in 3 ml of water was added, and then the mixture rendered alkaline by adding a solution of 1.45 g (0.036 mole) of sodium hydroxide in 2 ml of water. The mixture was refluxed for 10 minutes and then allowed to stand in a refrigerator overnight. The separated crystals were filtered off, washed with water and 60% cold ethanol and dried. 4.4 g (42%) of crude product, melting at 178°–183° C, were obtained. This sustance was recrystallized from 70 ml of ethanol to obtain 3.2 g (30%) of pure diastereomer "a"; m.p.; 180°–182° C.

b. 10 g (0.033 mole) of "b"-2-oxo-3,4-cyclopentano-9,10-dimethoxy-1,2,3,4,6,7-hexahydro-11bH-benzo[a]quinolisine were added at 80° to 90° C to a stirred solution of 20 g of hydroxylamine hydrochloride in 200 ml of water. The mixture was stirred at the same temperature for an additional 30 minutes and then cooled to 20° C. The separated crystalline substance was filtered off and washed with water. The resultant 10.2 g of hydrochloride salt, m.p.: 183°–185° C, were dissolved in 70 ml of 50% aqueous ethanol with heating, and the pH of the solution adjusted to between 9 and 10 by adding about 10 ml of 20% aqueous sodium hydroxide solution. The separated crystals were filtered off and washed with water. 7.35 g (70%) of diastereomer "b" were obtained; m.p.: 208°–210° C. After recrystallization from tenfold amount of dioxane, the product melted at 211°–213° C.

The hydrogen maleate of the above compound was prepared as follows: One part of maleic acid and two parts of diastereomer "b" were dissolved in 50-fold amount of refluxing 98% ethanol. The solution was allowed to cool and the crystals separated. The crude salt, obtained with a yield of 80%, melted at 173°–175° C. After recrystallization from 98% ethanol, the product melted at 173°–175° C.

Analysis:
calculated for $C_{18}H_{24}N_2O_3$ (M = 316.40):
C: 68.33%, H: 7.64%, N: 8.85%;
found: C: 68.59%, H: 8.26%, N: 8.85% (isomer "a")
C: 67.69%, H: 7.93%, N: 9.04% (isomer "b").
IR-spectrum (cm$^{-1}$):

|  | isomer "a" | isomer "b" |
| --- | --- | --- |
| hydroxy group | 3280 (diffuse) | 3190,3080 (diffuse) |
| imino group | 1670 (very weak) | 1670 (very weak) |
| aromatic skeletal vibration | 1615,1520 | 1615,1530 |
| Bohlmann-bands | 2760,2820 | — |
| —OCH₃ symmetric stretching | 2840 | 2840 |
| —CH₂ symmetric stretching | 2880 | 2880 |
| —CH₂ asymmetric stretching | 2920,2945 | 2920,2945 |
| —OCH₃ asymmetric stretching | 2975 | 2975 |
| NMR-spectrum (δ values): | isomer "a" | isomer "b" |
| 8-H, 11-H | 6.55, 6.70 | 6.55, 6.70 |
| 9,10-OCH₃ | 3.80 | 3.80 |
| 2-N-OH | 9.50 | — |

EXAMPLE 13

2-Hydroxyimino-3,4-cyclohexano-9,10-diethoxy-1,2,3,4,6,7,-hexahydro-11bH-benzo[a]quinolisine a. 20 g (0.058 mole) of "b"-2-oxo-3,4-cyclohexano-9,10-diethoxy-1,2,3,4,6,7-hexahydro-11bH-benzo[a]-quinolisine, a compound prepared according to the process described in Example 1, were added at 90° to 100° C to a stirred solution of 40 g of hydroxylamine hydrochloride in 350 ml of water. The mixture was stirred at the same temperature for 10 minutes and then cooled to 25° C. The separated crystals were filtered off, washed three times with 30 ml of water and dried. 23 g of the hydrochloride walt were obtained; m.p.: 178°–181° C. This substance was dissolved in 200 ml of 50% ethanol with heating and the solution rendered alkaline (pH = 9) with 20% aqueous sodium hydoxide solution. The mixture was cooled to 35° C. The separated crystals were filtered off, washed three times with 40 ml of water and dried. 17.8 g (86%) of crude diastereomer "b" were obtained; m.p.: 168°–170° C. After recrystallization from 700 ml of ethanol, 14.4 g (70%) of purified substance were obtained; m.p.: 178°–180° C.

b. the mother liquor containing crude diastereomers "b" and "c" was diluted with equal volume of water and the mixture cooled to 0° C. The separated crystals, weighing 1.1 g, were filtered off and recrystallized twice from ethanol. 0.55 g of diastereomer "c" were obtained; m.p. 178°–183° C.

Analysis:

calculated for $C_{21}H_{30}N_2O_3$ (M = 358.47):
C: 70.36%, H: 8.44%, N: 7.82%;
found: C: 70.33%, H: 8.78%, N: 7.74% (isomer "b")
C: 70.01%, H: 8.54%, N: 8.08% (isomer "c").

IR-spectrum (cm⁻¹):

|  | isomer "b" | isomer "c" |
| --- | --- | --- |
| hydroxy group | 3270 (diffuse) | 3090, 3220 (diffuse) |
| imino group | 1680 (very weak) | 1665 (very weak) |
| aromatic skeletal vibration | 1610, 1520 | 1610, 1520 |

EXAMPLE 14

2-Hydroxyimino-3,4-cyclohexano-9,10-dimethoxy-1,2,3,4,6,7-hexahydro-11bH-benzo[a]quinolisine A mixture of 19.2 g (0.1 mole) of 6,7-dimethoxy-3,4-dihydro-sioquinoline, 25 ml of 1-acetyl-cyclohexene, 0.7 g of methylamine hydrochloride and 50 ml of ethanol was refluxed for 10 hours. The solvent was evaporated and the residue dissolved in 150 ml of benzene. The benzene solution was extracted in three portions with 180 ml of 10% aqueous hydrochloric acid. The acidic solutions were combined, decolorized without heating, filtered and neutralized (pH =7.5 to 8). The separated oily substance was extracted three times with 70 ml of benzene. The benzene solutions were combined and evaporated. 28.1 g (89.2%) of 2-oxo-3,4-cyclohexano-9,10-dimethoxy-1,2,3,4,6,7-hexahydro-11bH-benzo[a]quinolisine were obtained in the form of an isomeric mixture.

A solution of the above isomeric mixture in 80 ml of ethanol was added to a solution of 28.1 g of hydroxylamine hydrochloride in 280 ml of water, and the mixture refluxed for 5 minutes. The alcohol was distilled off and the separated crystals filtered off and washed with water. 14.5 g (39.7%) of 2-hydroxyimino-3,4-cyclohexano-9,10-1,2,3,4,6,7-hexahydro-11bH-benzo[a]quinolisine hydrochloride were obtained; the product contained 60% of isomer "a", 30% of isomer "b" and 10% of isomer "c". The aqeuous mother liquor was rendered alkaline (pH = 8 to 8.5), the separated substance filtered off, washed with water and dried. 5.9 g (16.1%) of 2-hydroxyimino-3,4-cyclohexano-9,10-dimethoxy-1,2,3,4,6,7-hexahydro-11bH-benzo[a]quinolisine were obtained which also contains 60% of isomer "a", 30% of isomer "b" and 10% of isomer "c".

EXAMPLE 15

2-Hydroxyimino-3,4-cyclohexano-5methyl-9,10-dimethoxy-1,2,3,4,6,7-hexahydro-11bH-benzo[a]-quinolisinium iodide a. 3.3 g (0.01 mole) of "b"-2-hydroxyimino-3,4-cyclohexano-5-methyl-9,10-dimethoxy-1,2,3,4,6,7-hexahydro-11-bH-benzo[a]quinolisine were dissolved in 50 ml of dimethyl formamide and 2 ml of methyl iodide were added to the solution. The mixture was maintained at 100° C for 5 hours. The solvent was evaporated uner reduced pressure and the residue triturated with a small amount of ethanol. The crystalline substance was filtered off and washed with ethanol. 3.6 (76%) of a crude quaternary salt were obtained; m.p.: 222°–229° C. The crude substance was recrystallized from a mixture of 50 ml of ethanol and 20 ml of water to obtain 1.85 g (39%) of pure "b"-2-hydroxyimino-3,4-cyclohexano-5-methyl-9,10-dimethoxy-1,2,3,4,6,7-hexahydro-11bH-benzo[a]quinolisinium iodide; m.p.: 239°–242° C.

Analysis:

calculated for $C_{20}H_{29}N_2O_3I$ (M = 472.36):
C: 50.86%, H: 6.18%, N: 5.93%, I: 26.87%;
found: C: 50.86%, H: 6.80%, N: 5.80%, I: 26.31%.

b. 3.3 g (0.01 mole) of "c"-2-hydroxyimino-3,4-cyclohexano-5-methyl-9,10-dimethoxy-1,2,3,4,6,7-hexahydro-11bH-benzo[a]quinolisine were dissolved in 50 ml of dimethyl formamide and 2 ml of methyl iodide added to the solution. The mixture was maintained at 100° C for 5 hours and then the solvent evapoated in vacuo. The residue was triturated with 50 ml of ethanol. The crystalline substance was filtered off and washed with a small amount of ethanol. 3.7 g (77%) of a crude substance melting at 252°–255° C were obtained. After recrystallization from a mixture of 50 ml of ethanol and 20 ml of water, 2.6 g (55%) of pure "c"-2-hydroxyimino-3,4-cyclohexano-5-methyl-9,10-dimethoxy-1,2,3,4,6,7-hexahydro-11bH-benzo[a]-quinolisinium iodide were obtained; m.p.: 244°–245° C.

Analysis:

calculated for $C_{20}H_{29}N_2O_3I$ (M = 472.36):

C: 50.86%, H: 6.18%, N: 5.93%, I: 26.87%;

found: C: 49.26%, H: 6.70%, N: 5.95%, I: 26.66%.

Although the invention has been described with reference to a plurality of preferred embodiments thereof, it is to be expressly understood that it is in no way limited by the disclosure of such a plurality of embodiments, but is capable of numerous modifications within the scope of the appended claims.

What is claimed is:

1. 2-Hydroxyimino-1,2,3,4,6,7-hexahydro-11bH-benzo-[a]quinolisine derivative of the general formula

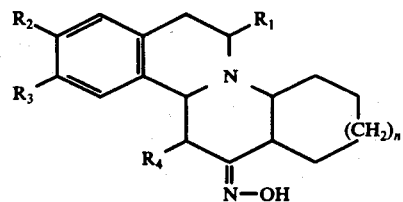

wherein $R_1$ and $R_4$ are each selected from the group consisting of hydrogen and an alkyl group of 1–4 carbon atoms, $R_2$ and $R_3$ are each selected from the group consisting of hydrogen, a hydroxyl group, an alkoxy group of 1–4 carbon atoms and an $R_2$–$R_3$ joint methylenedioxy group, and $n$ is an integer from 0–2.

2. "b"-2-Hydroxyimino-3,4-cyclohexano-9,10-dimethoxy-1,2,3,4,6,7-hexahydro-11bH-benzo[a]quinolisine.

3. "b"-2-Hydroxyimino-3,4-cyclohexano-9,10-diethoxy-1,2,3,4,6,7-hexahydro-11bH-benzo[a]quinolisine.

4. 6-Methyl-2-hydroxyimino-3,4-cyclopentano-1,2,3,4,6,7-hexahydro-11bH-benzo[a]quinolisine hydrochloride.

5. 2-Hydroxyimino-3,4-cyclopentano-9-methoxy-10-hydroxy-1,2,3,4,6,7-hexahydro-11bH-benzo[a]quinolisine hydrochloride.

6. 2-Hydroxyimino-3,4-cyclohexano-5-methyl-9,10-dimethoxy-1,2,3,4,6,7-hexahydro-11-bH-benzo[a]quinolisinium iodide.

* * * * *